United States Patent
Maase et al.

(10) Patent No.: US 7,084,298 B2
(45) Date of Patent: Aug. 1, 2006

(54) METHOD FOR PRODUCING N-PHOSPHONOMETHYL IMINODIACETIC ACID

(75) Inventors: Matthias Maase, Speyer (DE); Michael Drögemüller, Mannheim (DE)

(73) Assignee: BASF Aktiengesellschaft, Ludwigschafen (DE)

( * ) Notice: Subject to any disclaimer, the term of this patent is extended or adjusted under 35 U.S.C. 154(b) by 288 days.

(21) Appl. No.: 10/451,740

(22) PCT Filed: Jan. 11, 2002

(86) PCT No.: PCT/EP02/00225

§ 371 (c)(1), (2), (4) Date: Jun. 25, 2003

(87) PCT Pub. No.: WO02/055527

PCT Pub. Date: Jul. 18, 2002

(65) Prior Publication Data

US 2004/0063995 A1     Apr. 1, 2004

(30) Foreign Application Priority Data

Jan. 12, 2001   (DE) ................................ 101 01 293

(51) Int. Cl.
*C07F 9/22* (2006.01)
*C07F 9/28* (2006.01)

(52) U.S. Cl. ........................ 562/17; 562/502; 562/571; 562/14; 562/554

(58) Field of Classification Search ................ 562/17, 562/502, 571, 14, 554
See application file for complete search history.

(56) References Cited

U.S. PATENT DOCUMENTS

| | | | | |
|---|---|---|---|---|
| 3,288,846 A | | 11/1966 | Irani et al. .................. 260/500 |
| 4,724,103 A | * | 2/1988 | Gentilcore .................... 562/17 |
| 4,775,498 A | | 10/1988 | Gentilcore ................ 260/502.5 |
| 5,312,972 A | * | 5/1994 | Cullen .......................... 562/17 |
| 5,312,973 A | * | 5/1994 | Donadello .................... 562/17 |
| 5,688,944 A | * | 11/1997 | Baysdon et al. .............. 562/17 |
| 5,688,994 A | * | 11/1997 | Baysdon et al. .............. 562/17 |
| 5,986,128 A | * | 11/1999 | Smith .......................... 562/17 |

FOREIGN PATENT DOCUMENTS

| | | |
|---|---|---|
| DE | 199 09 200 | 8/2000 |
| EP | 0 155 926 | 8/1988 |
| EP | 0 595 598 | 5/1994 |
| EP | 0 618 212 | 10/1994 |
| GB | 2021589 | 12/1979 |
| GB | 2154588 | 9/1985 |
| WO | WO 94/15939 | 7/1994 |
| WO | WO 96/40698 | 12/1996 |
| WO | WO 00/02888 | 1/2000 |
| WO | WO 00/14093 | 3/2000 |

* cited by examiner

*Primary Examiner*—Johann Richter
*Assistant Examiner*—Chukwuma Nwaonicha
(74) *Attorney, Agent, or Firm*—Jason D. Voight

(57) ABSTRACT

The present invention relates to a process for the preparation of N-phosphonomethyliminodiacetic acid by reacting an alkali metal salt of iminodiacetic acid with phosphorus trichloride in aqueous solution with formation of the hydrochloride of iminodiacetic acid, phosphorous acid and of the corresponding alkali metal chloride, followed by reaction with a formaldehyde source and, if desired, recovery of the N-phosphonomethyliminodiacetic acid from the reaction mixture, in which water, which may comprise HCl, is removed from the reaction mixture during and/or after reacting the alkali metal salt of iminodiacetic acid with phosphorus trichloride until the concentration of iminodiacetic acid hydrochloride is at least 40% by weight, based on the weight of the reaction mixture minus the weight of alkali metal chloride.

The process makes possible the preparation of N-phosphonomethyliminodiacetic acid in a simple fashion and in high yield.

8 Claims, No Drawings

METHOD FOR PRODUCING N-PHOSPHONOMETHYL IMINODIACETIC ACID

The invention relates to a process for the preparation of N-phosphonomethyliminodiacetic acid (PMIDA) by reacting an alkali metal salt of iminodiacetic acid (IDA) with phosphorus trichloride in aqueous solution with formation of the hydrochloride of iminodiacetic acid, phosphorous acid and of the corresponding alkali metal chloride, followed by reaction with a formaldehyde source.

As is known, PMIDA is an intermediate for the preparation of the nonselective herbicide N-phosphonomethylglycine (glyphosate). A number of processes for the preparation of PMIDA by phosphonomethylation of IDA have already been described. Some of these processes start from IDA in the form of the free acid. Thus, DE 2914294 A discloses the reaction of IDA with phosphorus trichloride and formaldehyde. This leads to a relatively high yield. However, the disadvantage of the process is that a large excess of phosphorus trichloride and formaldehyde must be employed. WO 94/15939 describes the reaction of IDA with phosphorous acid and a formaldehyde source in aqueous solution in the presence of concentrated sulfuric acid. In order to obtain satisfactory yields, the filtrates obtained in the recovery of PMIDA are subjected to complicated work-up.

EP 618212 A (which corresponds to U.S. Pat. No. 5,312,973) describes the preparation of PMIDA by phosphonomethylation of IDA with an aqueous solution of phosphoric acid and hydrochloric acid, and also formaldehyde. This aqueous solution is prepared before the phosphonomethylation by hydrolyzing phosphorus trichloride with water or hydrochloric acid, the reaction temperature and the amount of water being regulated in such a way that hydrochloric acid and phosphorous acid are present in the aqueous solution in a molar ratio of 0.5:1 to 2:1. The process is thus carried out with substoichiometric amounts of hydrochloric acid. Furthermore, the phosphonomethylation is carried out in such a way that IDA and phosphorous acid are present in a molar ratio of between 1:1 and 1:1.2. This complicated and tedious process gives PMIDA in a yield of 91%.

Other processes start from an alkali metal salt, in particular the disodium salt (DSIDA) of IDA. Thus, WO 96/40698 (which corresponds to U.S. Pat. No. 5,688,994) describes a process for the preparation of PMIDA by simultaneously introducing an IDA source, a formaldehyde source and a source for phosphorous acid into the reaction mixture. Substances which can be used as IDA source are an alkali metal salt or the salt of a strong mineral acid of IDA or IDA in the form of the free acid. The yield of 87% achieved in this process is not satisfactory.

EP 595598 A describes the preparation of hydroxymethyliminodiacetic acid by reacting an alkali metal salt of IDA with a formaldehyde source. This is followed by the reaction of the resulting hydroxymethyliminodiacetic acid with phosphorous acid in the presence of hydrochloric acid. The route via hydroxymethyliminodiacetic acid as intermediate was chosen in order to obtain a storage-stable starting solution for the preparation of PMIDA. In contrast to hydroxymethyliminodiacetic acid, the disodium salt of IDA precipitates upon storage in the form of crystals and causes difficulties upon subsequent processing.

WO 00/14093 describes a process for the preparation of PMIDA by reacting a metal salt of IDA with such an amount of a mineral acid which is required for the formation of IDA, addition of a source for phosphorous acid in order to obtain a solution of the phosphite salt of IDA, separation of the metal salt present in the reaction mixture of the strong mineral acid used for forming IDA from the solution of the phosphite salt of iminodiacetic acid, and phosphonomethylation of the phosphite salt with a source for phosphorous acid and a formaldehyde source in the presence of a strong mineral acid. While this process gives a relatively high yield, it is complicated because it encompasses two additional reaction steps, viz. the formation of the phosphite salt of IDA, and the separation of the abovementioned metal salt. A similar process is described in WO 00/22888.

Finally, EP 155926 A (which corresponds to U.S. Pat. Nos. 4,724,103 and 4,775,498) describes a process for the preparation of PMIDA by reacting an alkali metal salt of IDA with a strong mineral acid with formation of the mineral acid salt of IDA, followed by phosphonomethylation with formaldehyde and phosphorous acid. Phosphorous acid and hydrochloric acid, being a strong mineral acid, can be provided by hydrolyzing phosphorus trichloride. Following the phosphonomethylation, aqueous NaOH is added to the reaction mixture in order to dissolve off the alkali metal salt of the strong mineral acid, which salt is present in the reaction mixture, so that PMIDA can be obtained as precipitate. The yield achieved with this process is not satisfactory.

DE 19909200 describes a process for the preparation of PMIDA by reacting IDA with phosphorous acid and formaldehyde in aqueous solution in the presence of a strong mineral acid. The reaction is carried out at a temperature of 110–150° C. and under protective gas atmosphere.

Further processes for the preparation of PMIDA are described in GB 2154588 A and U.S. Pat. No. 3,288,846.

The processes described in the prior art share the fact that they are complicated, for example because they encompass additional reaction steps, such as neutralization of the alkali metal salt of IDA, and/or that the yields leave something to be desired.

It is an object of the present invention to provide a process which yields PMIDA in a simple fashion and in high yield.

We have found that this object is achieved when water, which may comprise HCl, is removed from the reaction mixture during and/or after reacting an alkali metal salt of IDA with phosphorus trichloride until the IDA·HCl concentration is at least 44% by weight.

The invention therefore relates to a process for the preparation of N-phosphonomethyliminodiacetic acid by reacting an alkali metal salt of iminodiacetic acid with phosphorus trichloride in aqueous solution with formation of the hydrochloride of iminodiacetic acid, phosphorous acid and of the corresponding alkali metal chloride, followed by reaction of the reaction product with a formaldehyde source, in which water, which may comprise HCl, is removed from the reaction mixture during and/or after reacting the alkali metal salt of IDA with phosphorus trichloride until the concentration of iminodiacetic acid hydrochloride is at least 44% by weight, based on the weight of the reaction mixture minus the weight of alkali metal chloride, and, if desired, the N-phosphonomethyliminodiacetic acid is recovered from the reaction mixture.

The process according to the invention can be illustrated by the following equation, the disodium salt having been selected as the alkali metal salt of IDA:

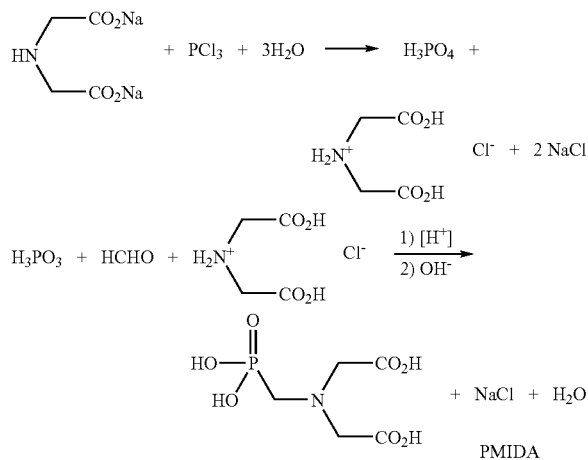

Substances which are used as the alkali metal salt of IDA are, in particular, the disodium and the dipotassium salts. The salts of iminodiacetic acid are usually prepared by hydrolyzing iminodiacetonitrile. The hydrolysate obtained can be employed as starting material for the process according to the invention. As an alternative, a salt which originates from other sources may also be employed. It is particularly preferred to employ the alkali metal salt of IDA in a purity of at least 90%.

In general, the alkali metal salt of IDA is employed in aqueous solution in a concentration of from 30 to 50% by weight, in particular from 35 to 45% by weight.

Phosphorus trichloride is added to the aqueous soluton of the alkali metal salt of IDA. The phosphorus trichloride hydrolyzes with formation of phosphorous acid and HCl, the latter of which reacts with the alkali metal salt of IDA with formation of the hydrochloride of IDA and of the corresponding alkali metal chloride. Phosphorus trichloride is preferably used in an amount of from approximately 1 to 1.2 molar equivalents (based on the alkali metal salt of IDA). When using more than one molar equivalent, excess HCl forms, which remains dissolved in the aqueous phase.

During and/or after the reaction of the alkali metal salt of IDA with phosphorus trichloride, water is removed from the reaction mixture, in particular by distillation under atmospheric pressure or reduced pressure (approximately 0.1 to 0.8 bar). When using more than one molar equivalent of phosphorus trichloride, the water which is removed from the reaction mixture comprises HCl. The water is preferably removed making use of the heat of the reaction of phosphorus trichloride with water. This reaction is strongly exothermic, and the heat of reaction which is given off suffices to halt the reaction mixture at the boil (under atmospheric pressure) and to remove the desired amount of water by distillation. As an alternative, at least some of the water can be removed by distillation after hydrolysis.

Since the phosphonomethylation which follows is carried out in the presence of acid, a strong mineral acid, in particular hydrochloric acid, can be added after the water has been removed. It is expedient to use an acid at a higher concentration, for example $\geq$20% by weight strength hydrochloric acid, in particular concentrated hydrochloric acid (30–37% by weight strength). The hydrochloric acid concentration in the reaction mixture prior to reaction with the formaldehyde source preferably amounts to 5 to 20% by weight, based on the amount by weight of water in the reaction mixture.

In accordance with the invention, such an amount of water is removed that the concentration of IDA·HCl in the reaction mixture before the phosphonomethylation is at least 40% by weight, based on the weight of the reaction mixture minus the weight of alkali metal chloride. Preferably, the concentration of IDA·HCl is in the range of from 44 to 55% by weight.

The phosphonomethylation is effected by reacting IDA·HCl with phosphorous acid and a formaldehyde source in the presence of acid. The purpose of the acid is to minimize the formation of N-methyliminodiacetic acid as by-product.

The formaldehyde source used is in particular an aqueous formaldehyde solution at a concentration of 30 to 50% by weight. As an alternative, paraformaldehyde may be used. It is preferred to use approximately 1.1 to 1.5 molar equivalents of formaldehyde. Using phosphorus trichloride in essentially equimolar amounts and the formaldehyde source in such an amount that approximately 1.3 to 1.45 molar equivalents of formaldehyde are available has proved to be particularly preferred.

In general, the reaction temperature is in the range of from approximately 85° C. to approximately 180° C., preferably from approximately 105 to approximately 145° C., and in particular from approximately 125 to approximately 145° C. The reaction can be carried out under atmospheric pressure or under moderate superatmospheric pressure, for example approximately 1.1–3 bar, either in the air or under protective gas.

Adding the formaldehyde source in two portions has proved to be particularly advantageous. First, most of the formaldehyde source, in particular 60 to 90% by weight, preferably 75 to 85% by weight, is added, while the remainder is added after a reaction time of approximately one hour. The overall reaction time generally amounts to 1.5 to 5 hours, in particular 2 to 3 hours. After phosphonomethylation, a suspension is present. In order to precipitate PMIDA and to dissolve the suspended alkali metal chloride, aqueous NaOH is added until the alkali metal chloride is in dissolved form. To precipitate PMIDA, a base is added to the solution up to not more than the isoelectric point (pH 1.3). Preferably, however, the pH is brought to a value of below the isoelectric point, in particular to a value in the range of from 0 to 1, preferably from 0.5 to 0.8. Surprisingly, it has emerged that the solubility of PMIDA is lower below the isoelectric point, the yield thus being increased.

The base used is an alkali metal hydroxide or alkaline earth metal hydroxide, preferably sodium hydroxide, in particular 15–25% by weight of aqueous sodium hydroxide solution. In order to obtain yields which are as high as possible, the pH is established, and/or the crystallization is effected, at as low a temperature as possible, for example at a temperature in the range of from 5° C. to 20° C.

The PMIDA which has separated out is recovered in the customary fashion, for example by filtration. If desired, the filter cake is washed with water.

Despite adjusting the pH and working at a low temperature during precipitation and crystallization, as mentioned above, a small amount of the PMIDA remains in the mother liquor and the wash water. This residual PMIDA can be recovered in the customary fashion, for example by evaporating the mother liquor and the wash water to dryness.

The process according to the invention can be carried out in customary reactors either continuously, semicontinuously or batchwise. If desired, the process can be carried out under protective gas atmosphere, for example under nitrogen or argon.

The process according to the invention has the advantage that PMIDA can be prepared in a simple fashion and in high yield. Nevertheless, the starting materials are employed only in a small molar excess. The starting materials can be employed in high concentration, and the suspension formed during the reaction of the alkali metal salt of IDA with phosphorus trichloride can still be handled with ease, despite the concentrated operation.

The examples which follow illustrate the invention without imposing any limitation.

EXAMPLE 1

554 g of water are introduced into a 1.6 l reactor equipped with turbine agitator (950 rpm) and baffle of the agitator. First, 203 g of NaOH (5.08 mol) and then 338 g of IDA (2.54 mol) are added with stirring and the mixture is refluxed, giving rise to a clear solution (disodium salt of iminodiacetic acid). This corresponds to 1095 g of a 41% strength solution of DSIDA in water. 348 g (2.54 mol) of $PCl_3$ are added in the course of one hour under reflux via a glass tube which is tapered toward the bottom and projects under the surface of the reaction mixture. The refluxing mixture is pumped into a 1.6 l stirred vessel equipped with impeller agitator (950 rpm) and baffle of the agitator and flushed with 50 g of $H_2O$. 411 g of a 2.8% strength HCl are distilled off from the reaction mixture. 194 g of 37% strength HCl are subsequently added to the reaction mixture, and 216 g of 49% strength formalin (3.55 mol) are metered below the surface of the reaction mixture in the course of one hour under reflux. Stirring is then continued for two hours under reflux and the contents of the reactor are transferred to a 2 l reactor equipped with a three-level cross-arm agitator (330 rpm) and precooled to a jacket temperature of 10° C. When the suspension has cooled to 26° C., 627 g of 20% strength NaOH (3.73 mol) are metered in under the surface of the reaction mixture in the course of 25 minutes so that the pH is 0.8. The suspension is pumped into a 2 l reactor equipped with anchor agitator (220 rpm), and stirring is continued for one hour at 15° C. The suspension is filtered through a glass-filter frit and washed with 250 g of $H_2O$. The PMIDA, which contains residual moisture, is dried in a vacuum drying oven at 80° C. and 50 mbar. The solid hold-up in the reactors is isolated by washing with 3320 g of 1.5% strength NaOH. The PMIDA content in the PMIDA crystallizate, in the wash solution, the mother liquor and the wash water is determined by means of HPLC. 541 g (2.38 mol) of PMIDA are obtained in total, which corresponds to a total yield of 94%. Of this, 4 g of PMIDA are present in the mother liquor and 1 g of PMIDA in the wash water. The total yield minus the PMIDA losses in the mother liquor and the wash water are defined as the isolated yield. It amounts to 93%.

Examples 2 to 5 which follow were carried out in a similar fashion, but using different amounts of starting materials and different concentrations. The results obtained are compiled in the table which follows.

| Example | g of $PCl_3$ | g of 49% strength formalin | Distilled off | g of 37% strength HCl added | Conc.[a] IDA * HCl | Total yield | Isolated yield |
|---|---|---|---|---|---|---|---|
| 2 | 402 | 184 | 323 g of 5.0% strength HCl | — | 47% | 94% | 92% |
| 3 | 384 | 184 | 434 g of 4.0% strength HCl | — | 54% | 95% | 92% |
| 4 | 384 | 216 | 301 g of 6.7% strength HCl | 47.7 | 44% | 91% | 90% |
| 5 | 348 | 216 | 431 g of 2.8% strength HCl | 200 | 45% | 93% | 91% |
| 6 | 348 | 216 | 412 g of 1.8% strength HCl | 200 | 44% | 93% | 88%[b] |

[a] calculated without NaCl
[b] too much PMIDA in the mother liquor owing to superneutralization

We claim:

1. A process for the preparation of N-phosphonomethyliminodiacetic acid, comprising
   a) reacting an alkali metal salt of iminodiacetic acid with phosphorus trichloride in aqueous solution to obtain the hydrochloride of iminodiacetic acid, phosphorous acid and the corresponding alkali metal chloride,
   b) halting the reaction mixture at the boil by the exothermic reaction of the phosphorous trichloride with water and removing a sufficient amount of water from the reaction mixture until the concentration of iminodiacetic acid hydrochloride is 44 to 55% by weight, based on the weight of the mixture minus the weight of alkali metal chloride,
   c) reacting with a formaldehyde source, and
   d) recovering the N-phosphonomethyliminodiacetic acid thus formed from the reaction mixture.

2. A process as claimed in claim 1, wherein the amount of HCl in the reaction mixture before the reaction with the formaldehyde source is brought to 5 to 20% by weight, based on the amount by weight of water in the reaction mixture.

3. A process as claimed in claim 1, wherein approximately 1.0 to 1.2 molar equivalents of phosphorus trichloride are used.

4. A process as claimed in claim 1, wherein the formaldehyde source is employed in such an amount that 1.0 to 1.5 molar equivalents of formaldehyde are available.

5. A process as claimed in claim 4, wherein the formaldehyde source is used in such an amount that 1.3 to 1.45 molar equivalents of formaldehyde are available.

6. A process as claimed in claim 1, wherein, to recover the N-phosphonomethyliminodiacetic acid, the pH of the reaction mixture is brought to not more than 1.3 by adding a base.

7. A process as claimed in claim 6, wherein the pH is brought to 0 to 0.8.

8. A process as claimed in claim 6, wherein 5 to 25% by weight strength sodium hydroxide solution is used as the base.

* * * * *